United States Patent [19]
Dan et al.

[11] Patent Number: 5,462,739
[45] Date of Patent: Oct. 31, 1995

[54] MICRODELIVERY DEVICE AND METHOD FOR ENHANCED DRUG ADMINISTRATION TO THE EYE

[75] Inventors: Jacov Dan, Hod Hasharon; Arieh Yaron, Rehovot, both of Israel

[73] Assignee: Yeda Research and Development Co., Ltd., Rehovot, Israel

[21] Appl. No.: 244,248

[22] PCT Filed: Nov. 16, 1992

[86] PCT No.: PCT/US92/09878

§ 371 Date: Nov. 2, 1994

§ 102(e) Date: Nov. 2, 1994

[87] PCT Pub. No.: WO93/09829

PCT Pub. Date: May 27, 1993

[30] Foreign Application Priority Data

Nov. 21, 1991 [IL] Israel ........................ 100112

[51] Int. Cl.$^6$ ........................................ A61F 2/00
[52] U.S. Cl. .................... 424/427; 424/94.67; 514/912; 514/913; 514/915; 606/6; 606/4; 604/8; 604/9; 604/10; 604/294; 351/245; 351/246; 356/125; 356/127
[58] Field of Search ................... 424/427, 94.67; 514/912, 913, 915; 606/6, 4; 604/8, 9, 10, 294; 351/245, 246; 356/125, 127

[56] References Cited

U.S. PATENT DOCUMENTS

| | | | |
|---|---|---|---|
| 3,302,646 | 1/1964 | Behney | 128/249 |
| 3,640,610 | 2/1972 | Nupuf | 351/13 |
| 3,869,206 | 3/1975 | Nupuf | 356/2 |
| 4,135,514 | 1/1979 | Zaffaroni et al. | 128/260 |
| 4,174,389 | 11/1979 | Cope | 424/94 |
| 4,674,503 | 6/1987 | Peyman et al. | 128/305 |
| 4,722,724 | 2/1988 | Schocket | 604/8 |
| 4,766,895 | 8/1988 | Reynolds | 128/303 |
| 4,826,478 | 5/1989 | Schocket | 604/8 |
| 4,844,093 | 7/1989 | Jampel et al. | 128/303 |
| 5,357,293 | 10/1994 | Uomori et al. | 351/209 |

Primary Examiner—Thurman K. Page
Assistant Examiner—Pamela S. Webber
Attorney, Agent, or Firm—Helfgott & Karas

[57] ABSTRACT

A device for pinpoint application of micro-quantities of a pharmacologically suitable composition to the outer hard coat of the eye, comprises a micro-container with a fixation element. The micro-container comprises a bore whose aperture is adapted to contact the eye surface, and the fixation element is adapted for reversibly adhering to the eye surface.

10 Claims, 3 Drawing Sheets

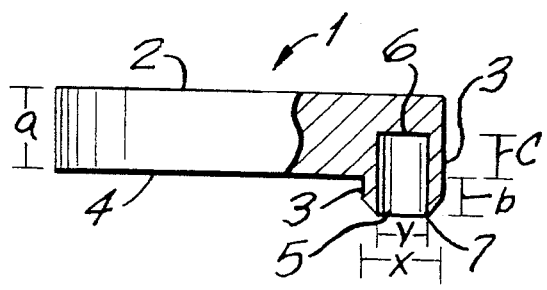
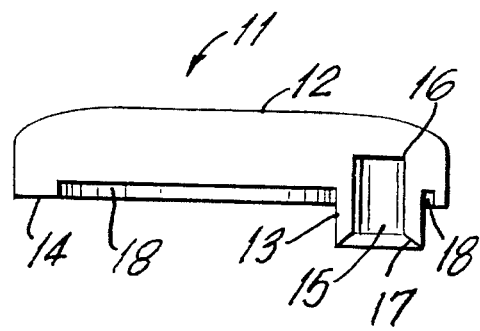
FIG.1a                FIG.2a
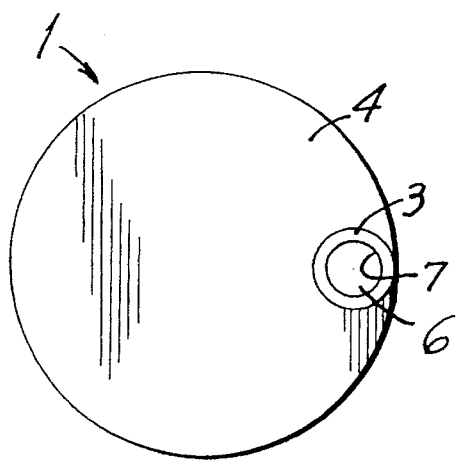
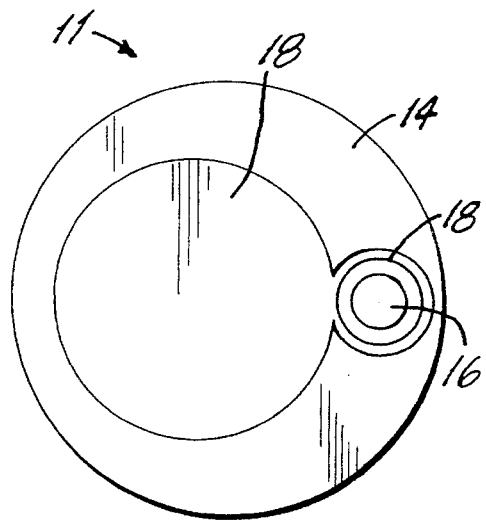
FIG.1b                FIG.2b

MICRODELIVERY DEVICE AND METHOD FOR ENHANCED DRUG ADMINISTRATION TO THE EYE

The present invention concerns a device and method of application for pinpoint delivery of micro-quantities of pharmaceutical compositions such as collagenase to a predetermined location on the outer hard coat of the eye, resulting in increased permeability at that location. The method is useful in the treatment of glaucoma when applied to the limbus, by increasing outflow facility. When treating other ocular disorders, the method may be applied at other locations of the sclera to enhance penetration into the eye of periocularly administered drugs.

BACKGROUND OF THE INVENTION

Collagen is the major constituent of the tissues forming the eye coat (Collagenase, Mandel, I. "Collagenase comes of age", p.1, Gordon and Breech, Science Publishers, Inc. 1972). Enzymes such as collagenase, which degrade collagen, are of importance in controlling conditions involving the collagen-rich tissue.

The use of enzymes in the medical field is well known. For example, alpha-chymotrypsin was used to lyse zonules in cataract surgery (I.C.C.E), hyaluronidase is used extraocularly as a means for spreading local anesthesia more effectively through tissue, and Tissue Plasminogen Activator has been proposed for clot-removal and filtering bleb reformation. The use of proteolytic enzymes as biopolymeric dry composition for treatment of wounds has been reported in U.S. Pat. No. 4,613,502. Detoxified agents such as enzymes obtained from snake venom have been used in the treatment of ocular disorders as disclosed in U.S. Pat. No. 3,869,548. Another bacterial extract, the toxin from Clostridium botulinus was proposed by Scott (J. Ped. Opthal. 17;21) in 1980 for use in ophthamology replacing strabismus surgery.

The use of collagenase has been disclosed in the art. Processes for production of collagenase from the bacterium Clostridium histolyticum have been disclosed in U.S. Pat. Nos. 3,705,083 and 3,821,364. Processes for preparing other collagenase preparations have been disclosed in U.S. Pat. Nos. 3,267,006 and 3,677,900. Collagenase has been used in the treatment of herniated intervertebral disc and such treatment is disclosed in U.S. Pat. No. 3,678,158. Use of collagenase as an adjunct to vitrectomy with membranectomy was proposed in U.S. Pat. No. 3,678,158. Use of collagenase has been described as an inhibitor of collagen-induced platelet aggregation and to be useful in selective degradation of collagen in the eye to remove scar tissue (European Patent Application No. 233,908). Collagenase obtained from Vibrio alginolyticus is said to be useful to prevent formation of deep scars during healing of burns and other lesions and has been proposed to treat dental caries, dental pulp and skin burns (U.S. Pat. No. 4,732,758). Soviet Union Patent No. 1,286,195 describes a method of treatment of glaucoma involving the formation of paths of outflow of intraocular fluid by direct injection of a proteolytic enzyme, leucozyme, into the sclera 3 mm posteriorly to the limbus.

The following brief discussion concerning basic ocular histology, anatomy and ophthalmic surgery serves to describe the collagen rich composition of the sclera and limbus, their involvement in ocular diseases such as glaucoma and the problems facing ophthalmic surgeons who are concerned with the treatment of it. Basically the hard outer layer of the mammal/an eyeball is formed by the opaque white sclera (83%) continued anteriorly by the cornea (16%) and posteriorly by the optic nerve sheath (<1%). These are densely collagenous hypocellular structures composed of (75%) of hydroxyproline-rich collagen, elastic tissue and mucopolysaccharides. The collagen fiber diameter varies between 28–300 nm with a periodicity of 64 nm. Embedded in mucopolysaccharide rich substance, the bundles are approximately parallel to the surface which in the cornea have a strict layering, responsible for its vital transparency. In the sclera and sclerocorneal junction the inner collagen bundles near, the Schlem canal are relatively inactive metabolically, having no intrinsic capillary bed and only a few fibrocytes. Between the transparent cornea anteriorly and the iris posteriorly is the anterior chamber which contains aqueous humor. The anterior chamber is directly connected with the small posterior chamber of the eye via the pupillary opening. Aqueous humor is secreted by cells of the ciliary body. This fluid flows into the posterior chamber and through the pupil into the anterior chamber, in order to nourish the cornea and maintain the internal ocular pressure. In humans, this aqueous fluid is formed at an approximate rate of 2.1 microliters/minute. The volume of the anterior chamber is 0.25 ml and this fluid which flows into the chamber is filtered out partially through the uveoscleral path (10–20%) but mainly through a system of channels in the trabecular meshwork (80–90%). The trabecular meshwork is a system of filters located in the angle of the anterior chamber under the sclerocorneal junction, the limbus. This meshwork consists of a collection of collagenous pillars which are lined by endothelial cells. It is the trabecular meshwork through which the aqueous fluid flows by entering a gradually enlarging system of collector channels to enter the aqueous veins and ultimately leave the anterior portion of the eye. Obstruction of this outflow system is thought to be the main reason for the increased intraocular pressure observed in glaucoma.

Movement of aqueous solution containing ions and solutes, smaller than or about equal in size to serum albumin, through the sclera results from a pressure difference between the suprachoroidal space where the pressure is about 1–2 mm Hg below the intraocular pressure and the episcleral venous pressure which approaches 10 mm Hg. This trans-scleral movement is slowed due to an eventual decrease in intraocular pressure and increases in pathologic cases such as glaucoma where the pressure is high.

Simple glaucoma is a genetically determined, age-related, ocular disease. It is one of the world's leading causes of blindness and in the U.S.A encompasses about 67,000 legally blind with an incidence of 5,500 new cases each year and 12% of all new cases of blindness. Glaucoma and directly related conditions account for 2 million suffers, 900,000 visually impaired, and 8.5% of all visits to an ophthalmologist, with a 440 million dollars direct and 1.9 billion dollars indirect health cost. (National Society for Prevention of Blindness, Vision Problems in U.S.A. Data Analysis 1980). It is rare in children but becomes increasingly prevalent with each decade over the age of 40 (0.4%–1.6%). Many more are at risk of developing glaucomatous loss of vision.

Glaucoma develops in two separate but related pathogenic stages. First, the ocular drainage of aqueous humor becomes impaired and the outflow facility decreases from about 0.3 to 0.05 microliter/minute/mmHg, establishing an inflow/outflow balance at a higher intraocular pressure. Second, the high intraocular pressure, aided by other less well defined pathogenic factors, causes compressive damage to fibers of the optic nerve head, and thereby insidious progression toward blindness due to loss of visual field.

Glaucoma is treated nonsurgically and surgically, both with the aim of achieving an increase in aqueous outflow or a decrease in its inflow with consequent lowering of intraocular pressure. In mild and moderate cases treatment is based upon long term topical application of drops of anti-glaucoma drugs, which however have a significant noxious effect as first reported by Barkan (Am. J. Opthamol.; 37:724) in 1954 and proven by histology of the tendon and the conjunctiva more than 30 years later. These effects obscure the prognosis of glaucoma surgery if eventually needed in the future as reported by Sherwood (Invest. Ophthal. Vis. Sci. 28 (suppl,135) in 1987. This encouraged clinical investigators to recommend surgery as the first stage of the glaucoma treatment (Migdal and Hitchings, Eye; 105653–656, 1986 and Lavin (Arch Ophthal; 108:1543 in 1990). When drug treatment fails, invasive methods such as filtration surgery, cryoablations and laser trabeculoplasty, are employed. Newer treatments still at a clinical investigative stage include intraoperative seton valve implantation, various types of laser surgery, thermal sclerostomy, ultrasonic disruption, and uncontrolled ocular injection of enzymes employed. All are accompanied by several drawbacks such as limited rate of success and even more, duraction of the effect (if any, in the case of ocular injection, according to Soviet Union Patent No. 1,286,195, since it was not reproducible under similar conditions in an animal model).

The following brief discussion concerning the most common complications of the supramentioned methods of glaucoma treatment is necessary to emphasize the need for the new method of treatment provided by the present invention, as detailed hereafter. The first choice when considering surgery is the angle laser treatment (trabeculoplasty). With this method it is possible to lower the intraocular pressure by increasing the outflow from the anterior chamber. In this treatment, small cicatrizing areas of about 60 microns, created with a chromatic laser, presumably enlarge the obstructed sclerotic trabecular pores. This treatment has various rates of success in different types of glaucoma and is especially low in juvenile and neovascular types. Furthermore, its effect is limited to two years and can be repeated only once. Other non mutilating surgical treatments are: Nd-Y.A.G. cyclophototherapy and cyclocryotherapy which may cause cataract and phthisis bulby and are therefore used only as a last resort at end-stage glaucoma, such as complicated, juvenile and neovascular types. Other methods such as Nd-Y.A.G. laser angle surgery, ultrasonic disruption, thermal sclerostomy, dye contact laser sclerostomy and internal sclerostomy with automated trephine are all still under investigation. Other techniques include the invasive and mutilating filtration surgeries that frequently fail on follow up (2 to 5 years) or necessitate in complicated cases, the use of large and partially toxic amounts of anti-metabolites, i.e. 5-fluorouracil and mitomycin or use of subconjunctivally implanted various seton valves. These procedures are repeatable only once (in special circumstances twice) and are associated with a wide range of complications such as sudden permanent loss of central vision, infection, malignant glaucoma, serious bleeding, flat anterior chamber (10%), failure of filtration (10%), technical problems, progression of glaucoma (15%) and progression of cataract (100%). The periocular injection of leucozyme (Soviet Union Patent Application No. 1286195) is particularly hazardous because a major part of the ocular region contains collagenous material. The uncontrolled injection of leucozyme and its unmonitored contact with any portion of the ocular region can risk continued vision in mammals and particularly in humans. Such injection cannot be directed to the limbus, since the nearby cornea would be severely damaged by lateral spreading of collagenase. Injection to the sclera in a more posterior location was found ineffective in lowering the intraocular pressure in rabbits using collagenase instead of the undefined leucozyme preparation.

SUMMARY OF THE INVENTION

The instant invention provides a solution to the many difficulties facing ophthalmologists engaging in the treatment of glaucoma by providing a device and method for augmenting controlled local limbal permeability with consequent increase of outflow facility accompanied by lowering of intraocular pressure, which is the aim of every glaucoma treatment. Furthermore, this invention provides a device and method for treatment of other ocular disorders by enhancing the penetration of large amounts of therapeutic agents continuously and in a controlled manner into the ocular cavity by means of direct contact with the sclera.

It is therefore the object of the present invention to provide a device and method for permeating small but effective amounts of pharmacologically suitable compositions into the eye non-invasively.

More specifically, it is the object of the invention to provide a device and method for pinpoint delivery of pharmacologically suitable compositions to the outer hard coat of the eye.

Another object of the invention is to provide a device and method for treating glaucoma.

A further object of the present invention to provide a device and method for pinpoint application of collagenase to the limbus.

Yet another object of the invention is to provide a method and device for safe application of the device to different locations on the limbus without adverse effects.

A still further object is to provide a method and device for repeated delivery of pharmaceutical compositions to the same location with the same device.

In accordance with this invention therefore, there is provided a device for pinpoint application of micro-quantities of a pharmacologically suitable composition to a preselected portion of the outer hard coat of the eye, said device comprising a micro-container with fixation means for reversible attachment of said micro-container to the outer hard coat of the eye adjacent to the preselected portion thereof, said micro-container comprising a pharmaceutical composition delivery bore whose aperture is adapted to contact the preselected portion of the outer hard coat of the eye so as to expose only the preselected portion thereof to the pharmaceutical composition.

A method for administering pharmaceutical compositions to the eye with the above device is also provided.

DETAILED DESCRIPTION OF THE DRAWINGS

The invention will best be understood with reference to the drawings in which

FIGS. 1a and 1b illustrate a cross-sectional and ventral plan view respectively of one embodiment of a device according to the invention;

FIGS. 2a and 2b illustrate a cross-sectional and ventral plan view respectively of an alternate embodiment of such a device;

DETAILED DESCRIPTION OF THE INVENTION

Figure 3B:
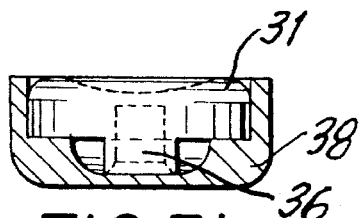
FIGS. 3a, 3b and 3c illustrate yet another embodiment of a pinpoint micro-container device with introducer.

The device of this invention will now be illustrated with reference to the drawings, which are not limiting but merely illustrative of the invention.

Referring now to FIGS. 1a and 1b, there is shown a device 1 according to the invention in the shape of a disc 2 having a diameter of about 5 mm. The height of the disc (a) is approximately 1 mm. From the ventral side 4 of the disc there extends a cylinder 3 having an outer diameter (x) of approximately 1 mm. The cylinder 3 extends about 0.5 mm (b) beyond the ventral side 4 of the disc. A bore 5 in the cylinder 3 has a diameter (y) of about 0.7 mm, which extends about 0.5 mm (c) into the disc 2 to provide a micro-container 6 with an internal volume of about 0.38 mm$^3$. The bottom edge 7 of the cylinder wall 3 is bevelled, coming to a point at its aperture in order to provide minimum contact surface where the micro-container contacts the eye.

In general, the micro-container should have a volume of preferably about 0.2 mm$^3$ to 1.5 mm$^3$ with a bore depth of about 0.5 mm to 1.5 mm. The aperture wall thickness should provide little surface contact with the sclera, and should preferably range from about 0.01 mm to 0.25 mm.

The device is used as follows. A suitable pharmaceutical composition, as for example collagenase either as a lyophilised powder or an aqueous solution containing a calcium salt, is introduced into the cylinder bore 5 which serves as a micro-container 6. The ventral side 4 of disc 2 is charged with histoacryl medical glue, which will adhere the disc to the sclera of the eye. The ventral surface of the disc is preferably made rough, so that the glue can better adhere thereto. With forceps or other gripping means, the disc is manipulated under the conjunctiva and over the surface of the scleral limbus of the eye, so that the micro-container 6 is brought into pinpoint contact with the desired area on the sclera and the glue contacts the sclera only adjacent the micro-container 6, assuring the adherence of the device 1 to the sclera for a given amount of time. The micro-container is thus in direct contact with the sclera in place. A collagenase composition can be applied via the micro-container at the sclero-corneal junction to augment sclero-limbal permeability and lower intra-ocular pressure.

Turning now to FIGS. 2a and 2b, there is shown another embodiment of the device 11 comprising a disc 12 and cylinder 13 which provides a micro-container 16. The bottom edge of the bevelled wall 17 provides a sharp aperture corresponding approximately to the outer diameter of the cylinder. In this embodiment, the ventral side 14 of the disc 11 comprises a recess 18 for holding the glue. It should be noted that the bevel 17 is at such an angle so that the aperture 15 has a larger diameter than the micro-container 16. This embodiment enables fixing the device on the sclera with minimal chances of the glue oozing into the micro-container 16 under the cylinder walls, since the glue can flow into the recess 18 and because of the sharp barrier formed by the bevelled edge.

Figure 3A:
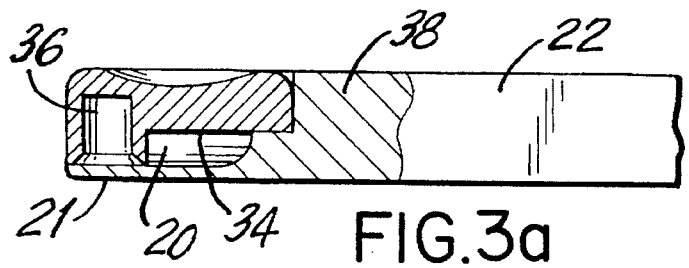
Figure 3C:
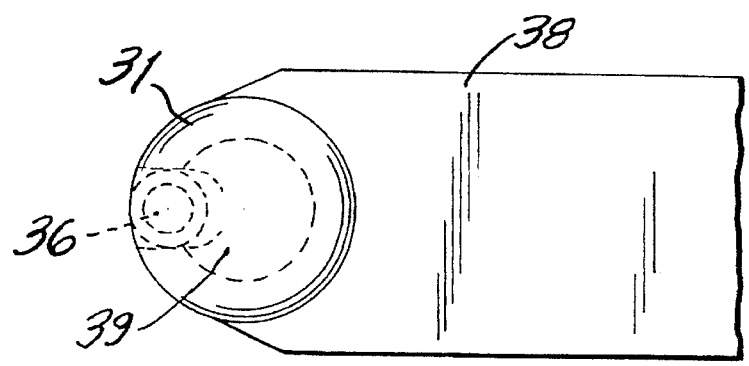

In FIGS. 3a, 3b and 3c there is shown another embodiment wherein the device comprising a disc 31 having an integral micro-container 36 with an introducer handle 38 releasably attached to the disc 31 with which to manipulate the micro-container into position on the sclera. Medical glue 20 is spread on the ventral side 34 of the disc. This device is used as follows. A 1 cm slit is made in the conjuctiva 1 cm posterior to the limbus and the micro-container 36 is inserted therein with the introducer 38. The micro-container 36 is placed in position at the limbus (when treating glaucoma) and the introducer handle 22 is removed while pressing down at the depression 39 of the dorsalodise of the disc 31 with a finger and pulling the introducer 38 back, thereby removing shield 21 from under the micro-container 36 and glue 20, thus contacting the sclera directly with the glue.

Figure 4B:
FIGS. 4a, 4b and 4c illustrate still another embodiment of the invention with a refillable micro-container and detachable fixation means.
Figure 4C:
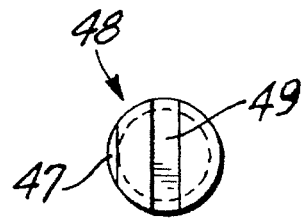
Figure 4A:
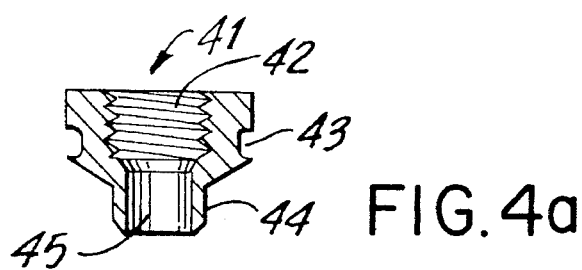

FIGS. 4a, 4b and 4c show yet another embodiment of the invention which comprises a micro-container consisting of a cylinder 41 having an outer diameter of about 2.0 mm and a threaded bore 42 of about 1.2 mm. A groove 43 circumferentially encompasses the cylinder 41. Extending from the cylinder 41 there is a narrower cylinder 44 having an outer diameter of about 1.0 mm and internal diameter 0.7 mm, providing a micro-container 45. The inner space of cylinder 44 is continuous with the threaded chamber 42 and provides a micro-container 45. A screw cap 48 (shown in FIGS. 4b and 4c) having a vertical groove 47 extending partly along its outer edge, is threaded through bore 42, thus fixing the volume of the micro-container 45. A depression 49 serves to insert a screwdriver for turning the screw cap 48. A silicone ring (not shown) is placed around the cylinder 41 and held in place in groove 43. This silicone ring serves as the fixation element to whose ventral side glue can be applied for adhering the micro-container to the sclera. The advantage of this particular embodiment is that the pharmaceutical composition can be introduced into the micro-container 45 through the open threaded bore 42 even after the device is glued in position, and subsequently capping the bore 42 with screw 48 of FIG. 4b. The purpose of groove 47 is to provide a vent for letting air out of the bore 42 while the screw 48 is being tightened to seal bore 42 completely with the screw 48. This embodiment also enables changing medication, for example collagenase neutralizing agent, or dosage while the device is still adhering to the sclera without removing it.

It is of course understood that although the examples use medical glue for adhering the fixation elements to the sclera, it is possible to use alternative methods, such as vacuum or thirsty glass for fixation means. In the latter case these would not be recessed with respect to the micro-container aperture, but would be flush therewith to be placed directly on the sclera.

Any pharmaceutical composition for treating the eye can be used with the device of the present invention. Such compositions may be liquids, gels or solids such as lyophilised powders. We have found this device particularly useful for the treatment of glaucoma by pinpoint application of collagenase.

The method of the instant invention is exemplified by experiments conducted on rabbits. The animal is stabilized in an examination restrainer cage, a pediatric lid retractor is introduced for eyelid stabilization and one drop of 0.4% oxybuprocain is instilled topically, for providing appropriate anesthesia to inhibit the brisk motion due to the pain reflex during application. For augmentation of aqueous outflow with consequent drop of intraocular pressure, a peritomy of about 3 mm is efectuated at the limbus and the said device, loaded with the said collagenase, is gently introduced on the limbus or within 1 mm from it to adhere by the said methods, and contact the limbal collagen for the required time interval in order to attain the necessary tissue thinning. Applications of the loaded device or direct injection of the said collagenase more than 2 mm posteriorly from the limbus, shows the same tissue alteration but without any influence on the intraocular pressure. Due to the safety and the ease of the invented method, reapplication can be carried out after immediate or delayed time intervals from the first intervention, if the desired effect on intraocular pressure is not achieved or diminishes too soon, respectively. Delivery and redelivery of the said collagenase to contact the tissue while the device is in a state of adherence is possible by filling-up the micro-container when using one of the invented embodiments.

The depth of enzymatic tissue degradation can be monitored throughout the period of application by means of ultrasonography, permitting removal of the device at the proper time. However, it is disclosed in the present invention that contact of 200 μg collagenase for 4 h' is the optimal time for achievement of the proper limbal thinning which allows augmented permeability and increment of outflow with consequent drop of intraocular pressure.

The tissue alteration caused by the application of the said collagenase by the method of the invention is demonstrated by histology of thin sections of the site of application at different time intervals after the application and found to have a unidirectional transscleral vectorial propagation of the collagenase effect, creating a base-up cone shape smooth walls tissue alteration. The duration of this effect is monitored by intraocular pressure measurements at due time intervals.

In the preferred embodiment of this invention, collagenase produced by the bacterium Clostridium histolyticum (clostridiopeptidase A) is used. This type of collagenase is commercially available from Advanced Biofactures Corporation and is sold as Collagenase (form III) and from Worthington, where it is sold as Collagenase (CLSPA). However any collagenase composition chromatographically purified by anion exchange (DE-52) and further by molecular sieving, having the main six collagenase isoenzymes, exhibiting its main activity on insoluble collagen substrate and having negligible activity of other proteases especially caseinase, are suitable and may be utilized in the practice of this invention. The said pharmaceutical composition can be used with the said device of the present invention. Such compositions may be a buffered solution of calcium acetate 10–33 mmolar, pharmacological gels well known in the art or, as preferred in the instant invention, lyophilized powders.

The cornea and the trabecular meshwork are lined with endothelial cells not allowing compounds with molecular weight greater than 6200 kDa to pass through the cell wall and contact the collagen fibers underneath. When the said collagenase, which has a molecular weight much greater than 6200 kDa, penetrates the anterior chamber in the amounts suggested for the said treatments, it does not significantly affect these structures. Another exposed structure in cases of penetration into the anterior chamber is the collagen rich iris protected evenly anteriorly by the pigmented anterior border layer. The risk of passage of eventual penetrated collagenase solution from the anterior chamber to the collagen-rich structures in the posterior segment is minimal since the thermal circulation of the aqueous washes the collagenase solution out of the eye through the new path formed by the treatment itself. Moreover, the aqueous was found to have intrinsic inhibitory properties on the collagenase used.

It is preferred that the flush solution used after removal of the micro-container to remove any trace of collagenase activity have a physiologic compatible pH of 7.40 and contain calcium chelator EDTA 0.5% as routinely used in ophthalmology. Rinsing should be carried out with an abundant amount of the said inhibitory solution, immediately after device removal, on all subpalpebral regions with special attention to the site of application. Moreover, the aqueous penetrating now in an enhanced manner through the site of application is capable of removing residual detrimental collagenase from the site and is noted to have intrinsic inhibitory properties upon the said collagenase activity.

The following experiments conducted in vitro on bovine sclera or in vivo on rabbits are exemplary. In all experiments the pharmaceutical composition shall refer to collagenase (CLSPA manufactured by Worthington). When used as solution the pharmaceutical composition was dissolved in buffer containing 50 mM Tris HCl, 10 mM Ca acetate pH 7.4. The device comprises the micro-container loaded with the said collagenase as solution, as lyophilized powder and as chemically immobilized enzyme, however it is within the scope of this invention to include other medications and pharmaceutical preparations used as solutions, lyophilized powder and chemically immobilized active substances. It is also within the scope of this invention to include other devices providing limited restricted and isolated area of contact between chemical composition and tissue.

EXPERIMENT 1

Figure 5:
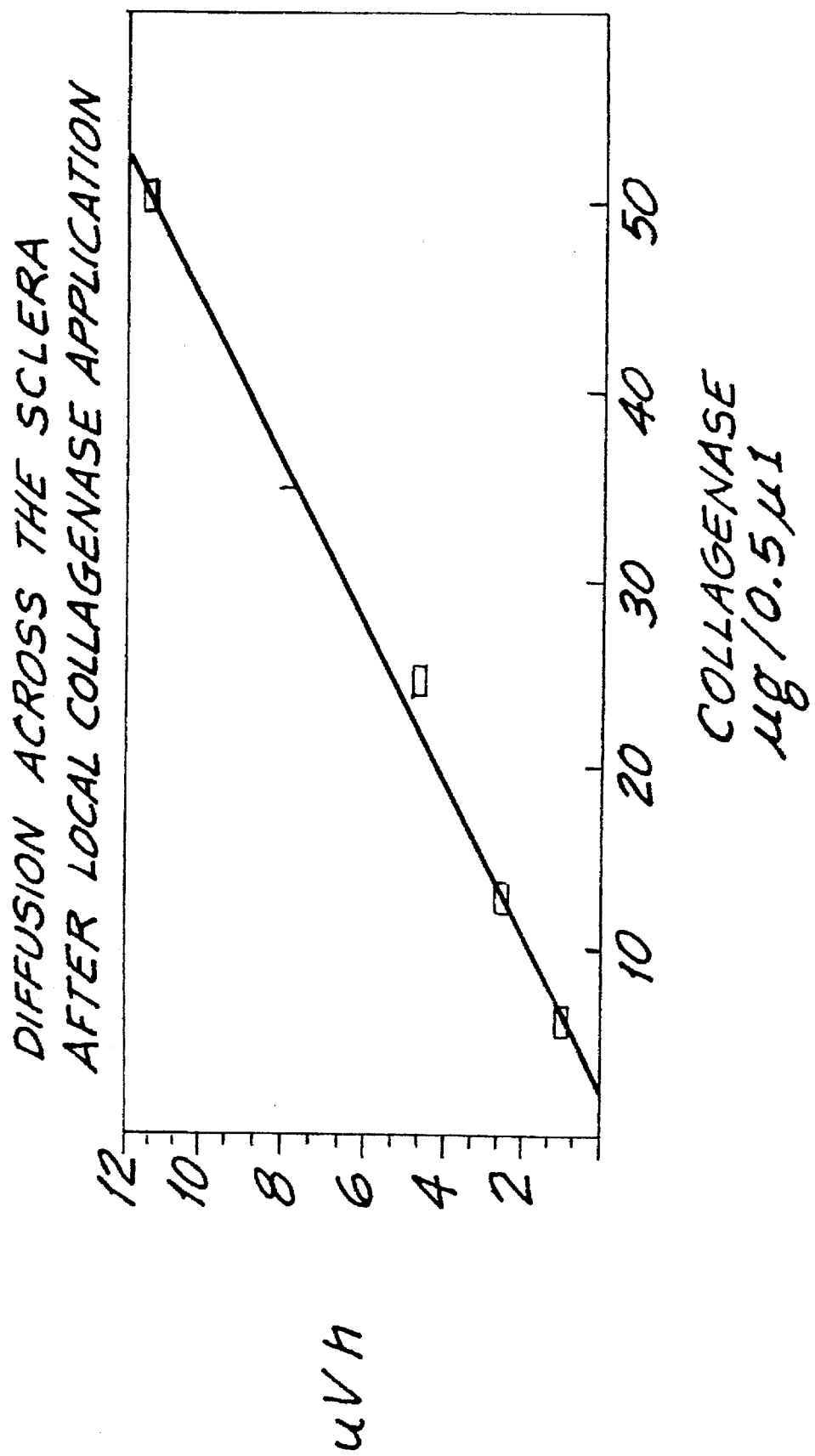
FIG. 5 is a graph showing the collagenase diffusion rate across the sclera.

The micro-container of the device in FIG. 1 was loaded with various concentrations of collagenase solution (up to 50 μg/0.5 μl—see FIG. 5), the ventral face of the metal plate around the micro-container was smeared with medical hystoacryl glue and applied to buttons of bovine sclera to adhere and contact the scleral collagen. After incubation in humid conditions at 37° C. for 16 hours, the device was removed and the tissue was rinsed with a solution of 70 mM EDTA. The scleral button was mounted in a "tissue permeability chamber" under pressure of 20 mmHg. The flow of liquid (phosphate buffered saline—PBS) through the scleral button was monitored by recording the waterhead decrease (initially 20 mmHg) in a calibrated pipet above the sclera, as well as measuring the volume collected underneath in the collector and was found to be 1.2–11.5 μl/h in accord with amounts of collagenase applied (0.5 μl, 6.25–50 mg/ml). The transscleral flow was calculated as 0.7 μl/μg collagenase/hour (FIG. 5). This result shows a substantial increase of the transscleral flow reached within the range of applicable amounts of commercial collagenase in comparison to the basic flow of 1 μl/hour through a control, enzymatically untreated, scleral button. The sites of the pinpoint application of collagenase were subsequently examined and these were found to have bore marks of 1 mm in diameter and deepness >75% of the tissue thickness. The bore had cone shape geometry with a round base at the site of application and smooth walls that gradually narrowed in the direction of the propagation of the collagenolytic effect. There was no lateral spreading on the surface and "intra-tissue" of the action of collagenase. This may be due to the scleral architecture characterized by highly organized collagen structure, by the design of the device and by the mode of isolation of application with the hystoacryl glue, which causes the unidirectional transscleral vectorial propagation of the enzymatic degradation.

EXPERIMENT 2

The micro-container of FIG. 1 was applied to the limbus of the right eye of an eight month white New Zealand rabbit. After 20 hours the animal was repositioned in the examination case for inspection and ocular manipulation. Temporary chemosis (conjunctival inflammatory response) was mild and diffuse and gradually disappeared within one week. There was no corneal damage, the anterior chamber was quiet, the pupilary response was normal and there was no change in the pre-application intraocular pressure. The device was removed with a Macpherson forceps, no scleral alteration was observed and the conjunctiva was reposited without sutures. This experiment shows the safety of using the device of this invention.

EXPERIMENT 3

To the limbus of each left eye of 3, four and half kg white New Zealand rabbits, 180±50 µg of the pharmaceutical composition of Experiment 1 was applied by means of the method of the invention through the said device (FIG. 2). As control, a similar device was mounted to the right eye by the said method without the pharmaceutical composition. The pre-application biomicroscopic examination was normal and the intraocular pressure was 15 mmHg. After 4 hours the device was removed and a survey of the eyes revealed similar features in all animals: In the left eye a mild conjunctival inflammatory response, and a brownish bore 1 mm in diameter. In the right eye a similar conjunctival inflammatory response was noticed without any scleral alteration (Example 2). The site of application was flushed with the said inhibitory solution. On follow-up the intraocular pressure in the left eye decreased by more than 50% in comparison to the right eye, during the first week. A meaningful decrease of intraocular pressure of about 30% continued for more than one month.

EXPERIMENT 4

The limbus of two rabbits was injected in about half the width of the tissue, with a solution (1.0 mg/ml) of the pharmaceutical composition of Experiment 1 (0.5 µl) by means of a Hamilton syringe (No. 7000,5). In the other eye buffer was injected in the same manner. On examination during the first day after the injection, both eyes were quiet and only in the eye injected with collagenase an area of filtration was formed by lysis of the collagen of a diameter of more than 0.5 cm invading the cornea where it appears cloudy and opaque. The effect of pressure decrease, of about 30%, was limited to one week. This direct limbal injection of collagenase was carried out in order to compare it with the method of the invention showing that even when small amounts were injected to the eye coat, the extent of spreading of collagen lysis is not controllable and the tissue was affected far beyond the site of injection extending to the cornea as well.

EXPERIMENT 5

In order to test the distance of effective application posterior to the limbus, the said device loaded with the same pharmaceutical composition as in Experiment 1 (1 µl, 50 mg/ml) was positioned to contact the scleral collagen with the orifice of the micro-container 3 mm posterior to the limbus. After 20 hours the device was removed disclosing an area of similar changes as previously described (Experiment 3) but without noting any difference in intraocular pressure from the untreated eye. Hence, increased permeability at a site distant from the limbus does not permit outflow of aqueous and is not useful for treatment of glaucoma.

EXPERIMENT 6

Direct injection of the pharmaceutical composition (0.05 µl 40 mg/ml) into the anterior chamber was carried out by means of a Hamilton syringe (No. 7000,5). The eye was inspected by biomicroscopy and the following minor changes were noted: a thin stream of blood, probably from the aqueous veins that in the rabbit are filled with blood, was observed on the corneal endothelial layer immediately after the injection. On the first day of follow-up, moderate inflammatory reaction was observed; ciliary injection restricted to the area of application, engorgement of iris vessels, with flare and cells in the normally deep anterior chamber. These signs decreased gradually and finally disappeared after one week. It is concluded that penetration into the anterior chamber with introduction of small amounts of the said pharmaceutical composition, did not elicit a major pathologic response.

EXPERIMENT 7

In order to test the possibility of delivery of collagenase solution while the device is in a state of adherence, a device (FIG. 4) was applied to the limbus of the left eye of a rabbit containing 50 µg of lyophilized collagenase powder. After two hours the stopper (4b) was removed and an additional amount of collagenase (0.5 µl 200 µg/µl) was injected by means of a Hamilton syringe into the micro-container, then the stopper was repositioned. The loaded device was left to contact the sclera for another two hours and was then removed. The scleral alterations observed were similar to those observed after a single application of the device with a sufficient amount of collagenase. The drop of intraocular pressure was similar to that seen after a single application. This data indicates that application and reapplication while the device is in a state of adherence is feasible.

EXPERIMENT 8

The possibility of a repeated intervention using the method of the invention was examined. Reapplication of the device was carried out to the limbus of the left eye of one rabbit in a location adjacent the area treated several months previously by the same method after return of the intraocular pressure to values of the control eye. The micro-container was loaded with 165 µg of the said pharmaceutical composition and the duration of application was 4 hours. The result was similar to the first application both macroscopically and functionally. The pressure decreased to 50% in comparison to the right eye for one week, then remained decreased to 30% for more than one month.

While the above experiments were conducted on rabbits, the results are indicative of what can be anticipated with all mammals. This invention may be practiced on any animal including a human.

A rabbit's occular region is similar to a human's in that both contain many collagen rich structures. The rabbit cornea, lens and anterior chamber is similar. The sclera's collagenous composition, although being similar, is thinner both in the single collagen fiber and in the total tissue thickness. Accordingly a different optimalization of amounts and time of application may be required in humans using the same device by the same method of enzyme-tissue contact, limitation and focalization.

In view of the preceding description, further modifications and alternative embodiments of the instant invention will be apparent to those skilled in the art. Accordingly, the preceding description is to be construed as explanatory and illustrative only and is for the purpose of teaching and enabling those skilled in the art to practice this invention. It should be understood that the suitable amount of pharmacological composition and the period of application may vary, as well as the predetermined area of application.

We claim:

1. A device for pinpoint application of micro-quantities of a pharmaceutical composition to a preselected portion of the outer hard coat of the eye, the device comprising a micro-container with fixation means for reversible attachment of said micro-container to the outer hard coat of the eye adjacent to the preselected portion thereof, said micro-container comprising a pharmaceutical composition delivery bore whose aperture is adapted to contact the preselected portion of the outer hard coat of the eye so as to expose only the preselected portion thereof to the pharmaceutical composition.

2. A device according to claim 1, wherein the micro-container and fixation means comprise a single unit.

3. A device according to claim 1, wherein the fixation means is separable from the micro-container.

4. A device according to claim 1, wherein the micro-container comprises a cylinder with a bore about 0.5 to 1.5 mm.

5. A device according to claim 1, wherein the micro-container has a volume of about 0.2 mm$^3$ to about 1.5 mm$^3$.

6. A device according to claim 1, wherein the micro-container comprises a removable stopper which enables filling the micro-container while it is in the state of adherence to the eye surface.

7. A device according to claim 1, wherein the thickness of a micro-container wall at its aperture is between 0.1 mm to 0.25 mm.

8. A non-invasive method for applying pharmaceutical compositions to a preselected portion of the outer hard coat of an eye at pinpoint locations, comprising the following steps:

providing a micro-container containing an amount of a pharmaceutical composition and having a pharmaceutical composition delivery bore; and reversibly attaching the micro-container to the outer hard coat of the eye so as to locate the delivery bore in contact with said preselected portion and thereby deliver the pharmaceutical composition solely to said preselected portion.

9. A method according to claim 8, wherein the micro-container is first placed on the desired location of the eye surface and fixed thereto and subsequently a pharmaceutical composition is introduced into the micro-container.

10. A method for treating glaucoma, comprising administering, at pinpoint location on the limbus of the eye for a given time, a sufficient amount of collagenase composition to effect limited controlled tissue degradation, thereafter neutralizing the collagenase and rinsing the eye, thereby decreasing the intraocular pressure.

* * * * *